(12) United States Patent
Lujan et al.

(10) Patent No.: US 9,289,144 B2
(45) Date of Patent: Mar. 22, 2016

(54) AUTOMATED 3D BRAIN ATLAS FITTING USING INTRA-OPERATIVE NEUROPHYSIOLOGICAL DATA

(75) Inventors: J. Luis Lujan, Cleveland, OH (US); Cameron C. McIntyre, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 2105 days.

(21) Appl. No.: 12/266,394

(22) Filed: Nov. 6, 2008

(65) Prior Publication Data
US 2009/0118635 A1 May 7, 2009

Related U.S. Application Data

(60) Provisional application No. 60/985,718, filed on Nov. 6, 2007.

(51) Int. Cl.
| | |
|---|---|
| A61B 5/04 | (2006.01) |
| A61B 6/00 | (2006.01) |
| G06T 3/00 | (2006.01) |
| G06T 7/00 | (2006.01) |
| A61B 5/00 | (2006.01) |
| A61B 5/055 | (2006.01) |
| A61B 6/03 | (2006.01) |
| A61N 1/05 | (2006.01) |

(52) U.S. Cl.
CPC .......... *A61B 5/04001* (2013.01); *A61B 5/4064* (2013.01); *A61B 6/5247* (2013.01); *G06T 3/0075* (2013.01); *G06T 7/0028* (2013.01); *A61B 5/055* (2013.01); *A61B 6/03* (2013.01); *A61N 1/0534* (2013.01); *G06T 2207/10088* (2013.01); *G06T 2207/30016* (2013.01)

(58) Field of Classification Search
None
See application file for complete search history.

(56) References Cited

FOREIGN PATENT DOCUMENTS

WO  WO 2004/096018 A2   11/2004

OTHER PUBLICATIONS

Rohde et al. IEEE Transactions on Medical Imaging, vol. 22, No. 11, 2003, p. 1470-1479.*
Dawant et al. Biomedical Image Registration. Lecture Notes in Computer Science, 2003, vol. 2717, 2003, 142-150.*
D'Haese et al. Medical Image Computing and Computer-Assisted Intervention—MICCAI 2005 Lecture Notes in Computer Science, 2005, vol. 3750, 2005, 427-434.*
Acar et al., "Safety Anterior Commissure-Posterior Commissure-Based Target Calculation of the Subthalamic Nucleus in Functional Stereotactic Procedures", *Stereotactic Funct. Neurosurg.*, 85:287-291, Aug. 2007.
Andrade-Souza, "Comparison of Three Methods of Targeting the Subthalamic Nucleus for Chronic Stimulation in Parkinson's Disease", *Neurosurgery*, 56:360-368, Apr. 2005.
Anheim et al., "Improvement in Parkinson Disease by Subthalamic Nucleus Stimulation Based on Electrode Placement", *Arch Neurol.*, 65:612-616, May 2008.
Butson et al., "Tissue and Electrode Capacitance Reduce Neural Activation Volumes During Deep Brain Stimulation", *Clinical Neurophysiology*, 116:2490-2500, Oct. 2005.
Butson et al., "Sources and Effects of Electrode Impedance During Deep Brain Stimulation", *Clinical Neurophysiology*, 117:447-454, Dec. 2005.
Butson et al., "Role of Electrode Design on the Volume of Tissue Activated During Deep Brain Stimulation", *J. Neural Eng.*, 3:1-8, published online Dec. 2005.
Butson et al., "Patient-Specific Analysis of the Volume of Tissue Activated During Deep Brain Stimulation", *NeuroImage*, 34:661-670, Jan. 2007.
Castro et al., "A Cross Validation Study of Deep Brain Stimulation Targeting: From Experts to Atlas-Based, Segmentation-Based and Automatic Registration Algorithms", *IEEE Transactions on Medical Imaging*, 25:1440-1450, Nov. 2006.
D'Haese et al., "Computer-Aided Placement of Deep Brain Stimulators: From Planning to Intraoperative Guidance", *IEEE Transaction on Medical Imaging*, 24:1469-1478, Nov. 2005.
Finnis et al., "Three-Dimensional Database of Subcortical Electrophysiology for Image-Guided Stereotactic Functional Neurosurgery", *IEEE Transactions on Medical Imaging*, 22:93-104, Jan. 2003.
Gross et al., "Electrophysiological Mapping for the Implantation of Deep Brain Stimulators for Parkinson's Disease and Tremor", *Movement Disorders*, 21:S259-S283, Jun. 2006.
Halpern et al., "Brain Shift During Deep Brain Stimulation Surgery for Parkinson's Disease", *Stereotact Funct. Neurosurg.*, 86:37-43, published online Sep. 2007.
Herzog et al., "Most Effective Stimulation Site in Subthalamic Deep Brain Stimulation for Parkinson's Disease", *Movement Disorders*, 19:1050-1099, published online Mar. 2004.
Jeon et al., A Feasibility Study of Optical Coherence Tomography for Guiding Deep Brain Probes, *Journal of Neuroscience Methods*, 154:96-101, Jun. 2006.
Khan et al., "Assessment of Brain Shift Related to Deep Brain Stimulation Surgery", *Sterreotact Funct. Neurosurg.*, 86:44-53, published online Sep. 2007.

(Continued)

*Primary Examiner* — Michael Borin
(74) *Attorney, Agent, or Firm* — Lowe Graham Jones PLLC; Bruce E. Black

(57) ABSTRACT

A method includes storing in memory preoperative brain atlas data. Neurophysiological data is obtained intra-operatively for a plurality of known sites in a brain of a given patient to provide corresponding intra-operative neurophysiological data for at least a portion of the sites. A constrained optimization is performed to fit the pre-operative brain atlas data based at least in part on the intra-operative neurophysiological data.

20 Claims, 11 Drawing Sheets

(56) References Cited

OTHER PUBLICATIONS

Koop et al., "Improvement in a Quantitative Measure of Bradykinesia After Microelectrode Recording in Patients with Parkinson's Disease During Deep Brain Stimulation Surgery", *Movement Disorders*, 21:673-678, published online Jan. 2006.

Lemaire et al., "Brain Mapping in Stereotactic Surgery: A Brief Overview from the Probabilistic Targeting to the Patient-Based Anatomic Mapping", *NeuroImage*, 37:S109-S115, available online Jun. 2007.

Machado et al., "Deep Brain Stimulation for Parkinson's Disease: Surgical Technique and Perioperative Management", *Movement Disorders*, 21:S247-S258, Jun. 2006.

Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.

Miocinovic et al., "Cicerone: Stereotactic Neurophysiological Recording and Deep Brain Stimulation-Electrode Placement Software System", *Acta Neurochir Suppl.*, 97:561-567, Dec. 2007.

Moran et al., "Real-Time Refinment of Subthalamic Nucleous Targeting Using Bayesian Decision-Making on the Root Mean Square Measure", *Movement Disorders*, 21:1425-1431, published online Jun. 2006.

Saint-Cyr et al., "Localization of Clinically Effective Stimulating Electrodes in the Human Subthalamic Nucleus on Magnetic Resonance Imaging", *J. Neurosurg.*, 97:1152-1166, Nov. 2002.

Sakamoto et al., "Homogeneous Fluorescence Assays for RNA Diagnosis by Pyrene-Conjugated 2'-O-Methyloligoribonucleotides", *Nucleosides, Nucleotides, and Nucleric Acids*, 26:1659-1664, online publication Oct. 2007.

Starr et al., "Implantation of Deep Brain Stimulators into the Subthalamic Nucleus: Technical Approach and Magnetic Resonance Imaging-Verified Lead Locations", *J. Neurosurg.*, 97:370-387, Aug. 2002.

Sterio et al., "Neurophysiological Refinement of Subthalamic Nucleus Targeting", *Neurosurgery*, 50:58-69, Jan. 2002.

Winkler et al., The First Evaluation of Brain Shift During Functional Neurosurgery by Deformation Field Analysis, *J. Neurol. Neurosurg. Psychiatry*, 76:1161-1163, Aug. 2005.

Yelnik et al., "Localization of Stimulating Electrodes in Patients with Parkinson Disease by Using a Three-Dimensional Atlas-Magnetic Resonance Imaging Coregistration Method", *J. Neurosurg,* 99:89-99, Jul. 2003.

Yelnik et al., "A Three-Dimensional, Histological and Deformable Atlas of the Human Basal Ganglia. I. Atlas Construction Based on Immunohistochemical and MRI Data", *NeuroImage,* 34:618,-638,Jan. 2007.

Gemmar et al., "Advanced Methods for Target Navigation Using Microelectrode Recordings in Stereotactic Neurosurgery for Deep Brain Stimulation", *21st IEEE International Symposium on Computer-Based Medical Systems,* Jun. 17, 2008, pp. 99-104, XP031284774.

Miocinovic et al., "Stereotactic Neurosurgical Planning, Recording, and Visualization for Deep Brain Stimulation in Non-Human Primates", *Journal of Neuroscience Methods*, 162:32-41, Apr. 5, 2007, XP022021469.

\* cited by examiner

AUTOMATED 3D BRAIN ATLAS FITTING USING INTRA-OPERATIVE NEUROPHYSIOLOGICAL DATA

RELATED APPLICATION

This application claims the benefit of U.S. Provisional Patent Application No. 60/985,718, which was filed on Nov. 6, 2007, and entitled AUTOMATED 3D BRAIN ATLAS FITTING USING MICROELECTRODE RECORDINGS, which is incorporated herein in its entirety.

GOVERNMENT FUNDING

This invention was made with government support under Grant Nos. R21 NS050449 and R01 NS059736 awarded by the National Institutes of Health. The U.S. government has certain rights in the invention.

TECHNICAL FIELD

The present invention relates generally to automated three-dimensional brain atlas fitting.

BACKGROUND

Deep brain stimulation (DBS) is a surgical treatment that uses high frequency electrical stimulation to reduce the symptoms of medically refractory neurological disorders, such as Parkinson's disease (PD), epilepsy and other neurological disorders. The surgical approach for PD DBS generally involves stereotactic targeting that combines multiple imaging modalities (e.g., magnetic resonance, computerized tomography, ventriculography) with standardized anatomical atlases and intraoperative electrophysiological mapping.

As an example, a stereotactic frame is placed on the patient's head parallel to the anterior commissural (AC)-posterior commissural (PC) line and the patient is taken for pre-operative magnetic resonance (MR) and computerized tomography (CT) imaging. A surgical target (e.g., subthalamic nucleus or other target) is determined from the pre-operative images. A safe electrode trajectory, oriented at a double oblique angle, is specified by defining arc and ring angles of the stereotactic frame (from the sagittal plane and anterior-posterior direction, respectively) that avoid the ventricles, sulci, and major arteries. A burr hole (e.g., 14 mm diameter) is made anterior to the coronal suture and approximately 12-30 mm lateral to the midline. A microelectrode is inserted through the opening and advanced toward the surgical target following the previously defined trajectory. As the microelectrode is advanced, recordings (MER) taken along the electrode track are used to identify brain nuclei based on their signal properties (e.g., firing rate and pattern, background signal, root mean square (RMS) value of the signal, responses to passive movements and external stimuli). Three to four tracks are typically required to map the boundaries of the target and identify regions of undesired side-effects.

Two-dimensional brain atlas slices superimposed on plots of the MER data are typically used to provide anatomical reference and aid in determining the optimal implantation location for the DBS electrode. However, the lack of oblique angles and limited spatial resolution between 2D atlas slices may result in inaccurate target localization, increasing the number of subsequent electrode tracks required to find the optimal DBS electrode location. In turn, neurosurgical navigation software systems have been introduced to overcome spatial resolution limitations and improve DBS electrode placement by combining MR/CT imaging and MER with 3D brain atlases that can be adapted to fit patient-specific neuroanatomy. Unfortunately, the typical application of brain atlas technology to DBS surgical planning consists of fitting the brain atlas to the pre-operative MRI to define an initial target location for electrode implantation. However, once the burr hole is drilled the intracranial pressure drops and the brain shifts, thereby altering the relative position of the target point and the stereotactic frame. Recent estimates suggest that subcortical structures can shift several millimeters during DBS surgery. In turn, a fundamental purpose of the MER data is to verify the stereotactic location of the target nucleus. However, current commercial surgical navigation systems either fail to provide an option to re-fit the brain atlas to MER data or require manual refitting, which is a tedious process that requires precious time in the operating room and may be inconsistent from user to user.

SUMMARY

The invention relates generally to fitting of a three-dimensional (3D) brain atlas based on electrophysiological data of a patient. The approach provides a method that can be performed intra-operatively by acquiring patient-specific intra-operatively obtained neurophysiological data. The approach can also be employed to help identify an optimal target implant location for a deep brain stimulation (DBS) electrode.

As a further example, a computer implemented method can store pre-operative brain atlas data. Neurophysiological data for a plurality of known sites in a brain of a given patient can be obtained intra-operatively obtaining to provide corresponding intra-operative patient-specific neurophysiological data. A constrained optimization is performed to fit the pre-operative brain atlas data to the intra-operative patient-specific neurophysiological data.

DETAILED DESCRIPTION

The invention relates generally to fitting of a three-dimensional (3D) brain atlas to intra-operative neurophysiological data obtained for a given patient. This method is capable of fitting a 3D brain atlas to the patient-specific neurophysiological data with approximately the same (or better) accuracy as trained neurophysiologists, but in a significantly less time, such as through the use of a personal computer or other processor based device. Furthermore, because the computer employs a consistent methodology to fit the atlas in the coordinate reference frame, random variability inherent to human involvement can be reduced. The approach described herein can utilize intra-operative neurophysiological data, individually or in combination other patient-specific data, to constrain the optimization method for fitting the brain atlas in a given coordinate system for a patient. For instance, some constraints for the optimization process can be obtained intra-operatively and other constraints can be obtained pre-operatively.

The approach can also be employed to help identify an optimal target implant location for a deep brain stimulation (DBS) electrode. Since the methodology is consistently applied for each patient, targets can be identified for multiple patients without the added variability of human influence.

Figure 1:
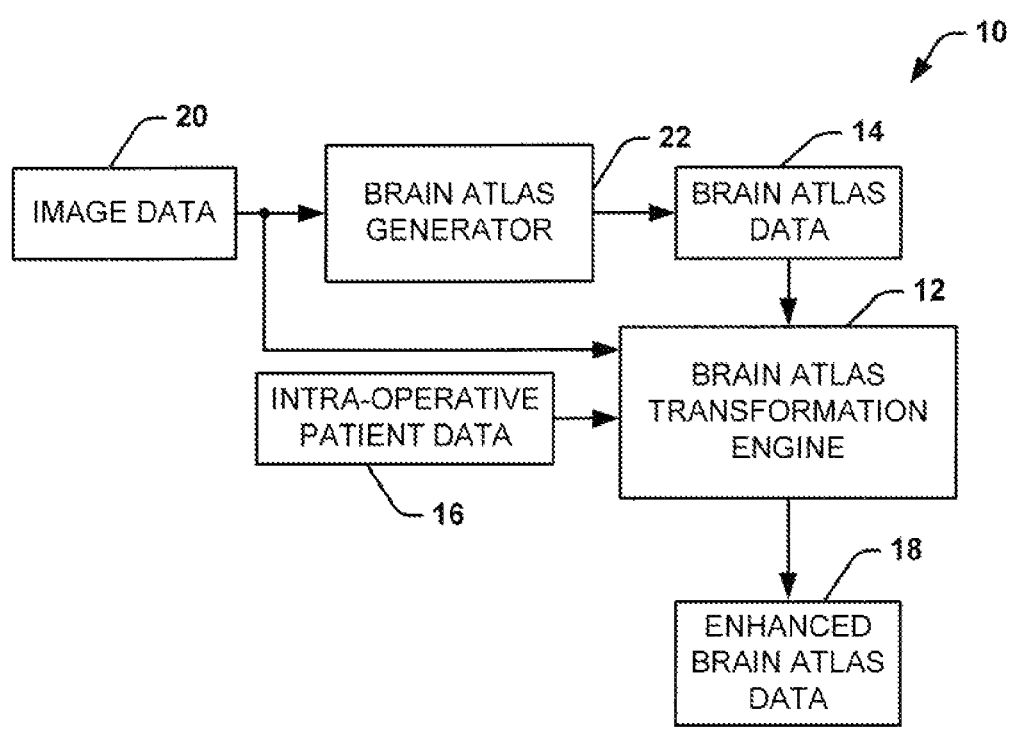
FIG. 1 depicts an example of a block diagram for fitting a three-dimensional brain atlas to intra-operative patient-specific data according to an aspect of the invention.

FIG. 1 depicts an example of a system 10 that can be employed to fit a brain atlas to intra-operative physiological data for a given patient according to an aspect of the invention. Briefly, the system 10 includes a brain atlas transformation engine 12 that is programmed to fit brain atlas data 14 to intra-operative patient data 16. The transformation engine 12 provides corresponding enhanced brain atlas data 18 based on the fitting implemented by the transformation engine 12. As described herein, the transformation engine 12 performs the fitting using an optimization method that is constrained at least in part on the intra-operative patient data.

The intra-operative patient data 16 can correspond to any data obtained during an operative procedure being performed on the patient that can help distinguish between anatomic structures or nuclei in the brain. As one example, the intra-operative patient data can include MER that have been classified as residing within a known anatomical structure of the brain. For instance, MER can be acquired as microelectrode device is advanced along a given trajectory relative to the stereotactic coordinate system of the patient. The MER data can be analyzed and classified to identify the nuclei in which the microelectrode resides for each recording. The classification can be performed by an automatic computer-executable method or manually by a human expert.

As another alternative, the intra-operative patient data 16 can be obtained from a cross-sectional imaging modality, such as optical coherence tomography (OCT). An explanation of how OCT can be utilized has been shown to be able to differentiate structures in a brain is explained in Jeon S W, Shure M A, Baker K B, Huang D, Rollins A M, Chahlavi A, Rezai A R, *A feasibility study of optical coherence tomography for guiding deep brain probes.* J Neurosci Methods, 2006 Jun. 30; 154 (1-2): pages 96-101, which is incorporated herein by reference.

The brain atlas data 14 can be provided to the system 10 as a predefined atlas or the brain atlas data can be generated as part of a pre-operative planning process. For example, the system 10 can employ patient specific image data 20 for the anatomical region of interest; namely, the brain. The imaging data 20 can be acquired according to any imaging modality capable of providing sufficient detail of anatomical features, such as magnetic resonance imaging (MRI), functional MRI, computed tomography (CT), positron emission tomography (PET) or other imaging techniques. The image data 20 can correspond to a segmented 3D representation of the patient's brain. Those skilled in the art will understand various well-known techniques and methods that can be employed to generate the image data 20.

The system can also include a brain atlas generator 22 is programmed to construct a patient-specific brain atlas from the image data 20, which defines the brain atlas data 104. The brain atlas generator 22 can be programmed to scales and reorients a predefined brain atlas model according to the patient-specific image data 116 to provide the atlas data 104. Those skilled in the art will understand and appreciate various techniques that can be utilized to construct a suitable brain atlas for use by the brain atlas transformation engine 102. For example, Surgical Navigation Technologies of Medtronic Inc. has developed a brain atlas that can be utilized to construct a 3D surface representation of the patient's brain including known anatomical structures (e.g., thalamus, subthalamic nucleus, corpus colossum and the like) based on image data 20. Other brain atlas generating software and neurosurgical planning tools are available from others, including Integra Radionics, Inc. and BrainLAB Inc., or software can be written to implement a brain atlas. It is to be understood that the brain atlas generator 22 can be part of an imaging system 114 or it can be a separate software module.

While the foregoing description describes that the optimization performed by the brain atlas transformation engine 12 is constrained by one or more type of intra-operative patient data 16, additional constraints, such as corresponding to segmented patient-specific image data or a model derived from the image data 20, can be utilized to augment the resulting transformation that is utilized to provide the enhanced brain atlas data 18. The brain atlas data 18 can be used to generate an intra-operative graphical display for a user, such as can be employed as part of planning tool for a target electrode trajectory. Because the algorithm implemented by the brain atlas transformation engine can be performed by personal computer in a short amount of time (e.g., less than two minutes on a Windows-based computer), for this technology affords clinical utility in the DBS surgical decision making process.

Figure 2:
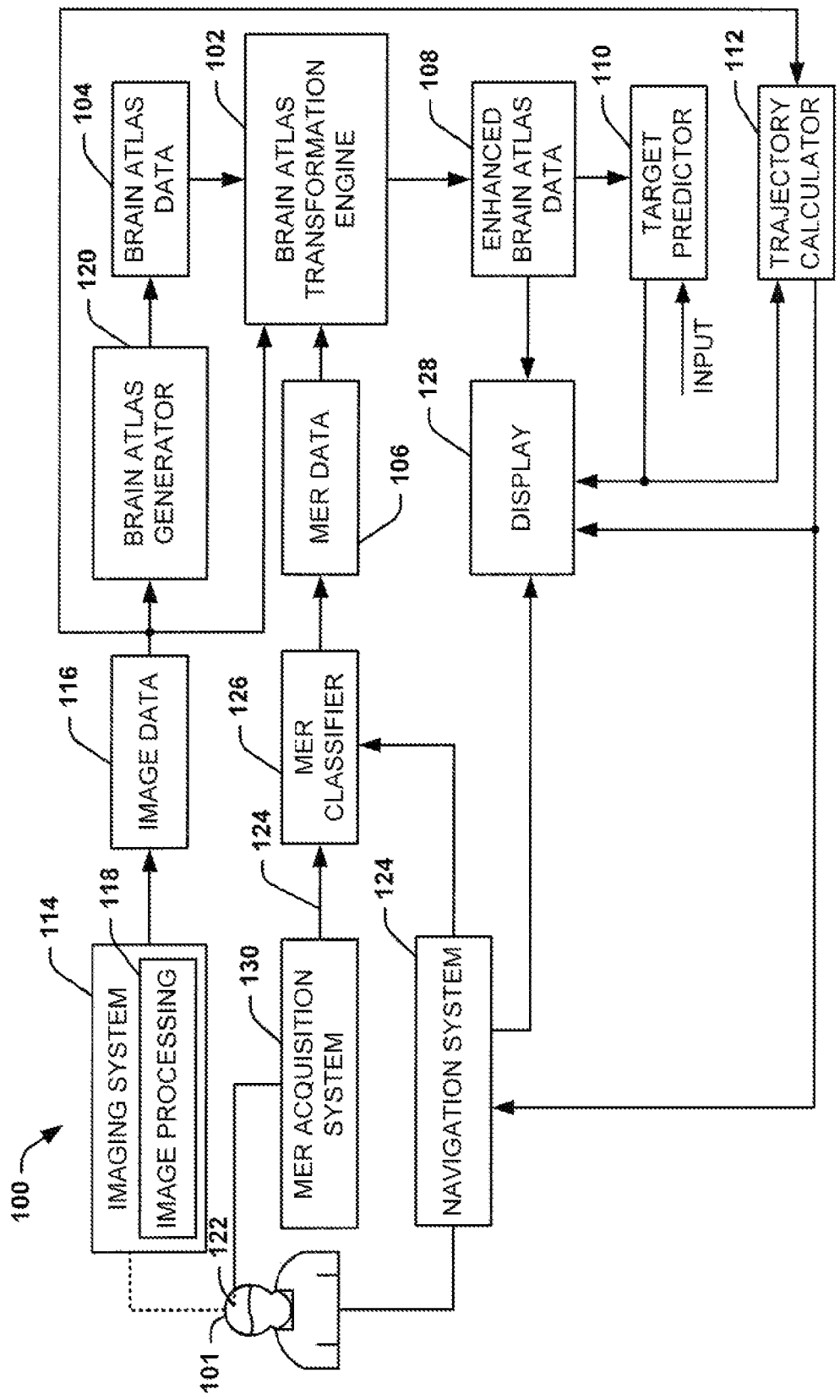
FIG. 2 depicts an example of a block diagram for fitting a three-dimensional brain atlas to MER data according to an aspect of the invention.

FIG. 2 depicts an example of a system 100 that can be employed to fit a brain atlas to electrophysiological data for a given patient 101 according to an aspect of the invention.

Some of the parts of the system 100 are similar to those shown and described in FIG. 1. Accordingly, when appropriate, reference can be made back to the description of FIG. 1 for additional information. The system 100 includes a brain atlas transformation engine 102 that is programmed to fit brain atlas data 104 to intra-operative patient data, which in the example of FIG. 2 is shown and described as MER data 106. The brain atlas transformation engine 102 generates corresponding enhanced brain atlas data 108 based on the fitting implemented by the transformation engine 102.

As described herein, the transformation engine 102 performs the fitting using a constrained optimization method. The resulting enhanced brain atlas data 108 can further be employed by a target predictor 110 to predict a target electrode location in the enhanced brain atlas. The predicted target electrode location can further be employed by a trajectory calculator 112 to determine a desirable trajectory or track for implanting the electrode at the target location.

The brain atlas data 104 can be provided to the system 100 as a predefined atlas or the brain atlas can be generated as part of a pre-operative planning process. For example, the system 100 can employ an imaging system 114 that is programmed and configured to provide image data 116 for the anatomical region of interest; namely, the brain. The imaging system 114 can be implemented according to any imaging modality capable of providing sufficient detail of anatomical features, such as described herein. Image processing 118 can be performed on the images to generate the image data 116 as a segmented 3D representation of the brain. Those skilled in the art will understand various well-known techniques and methods that can be employed to generate the image data 116 in an appropriate form for use in the system 100.

A brain atlas generator 120 is programmed to construct patient-specific brain atlas data 104 from the image data 116. The brain atlas generator 120, generally speaking, scales and reorients a predefined brain atlas model according to the patient-specific image data 116 to provide the atlas data 104. Those skilled in the art will understand and appreciate various techniques that can be utilized to construct a suitable brain atlas for use by the brain atlas transformation engine 102, such as described herein with respect to FIG. 1. It is to be understood that the brain atlas generator 120 can be part of the imaging system 114 or it can be a separate software module.

Figure 3:
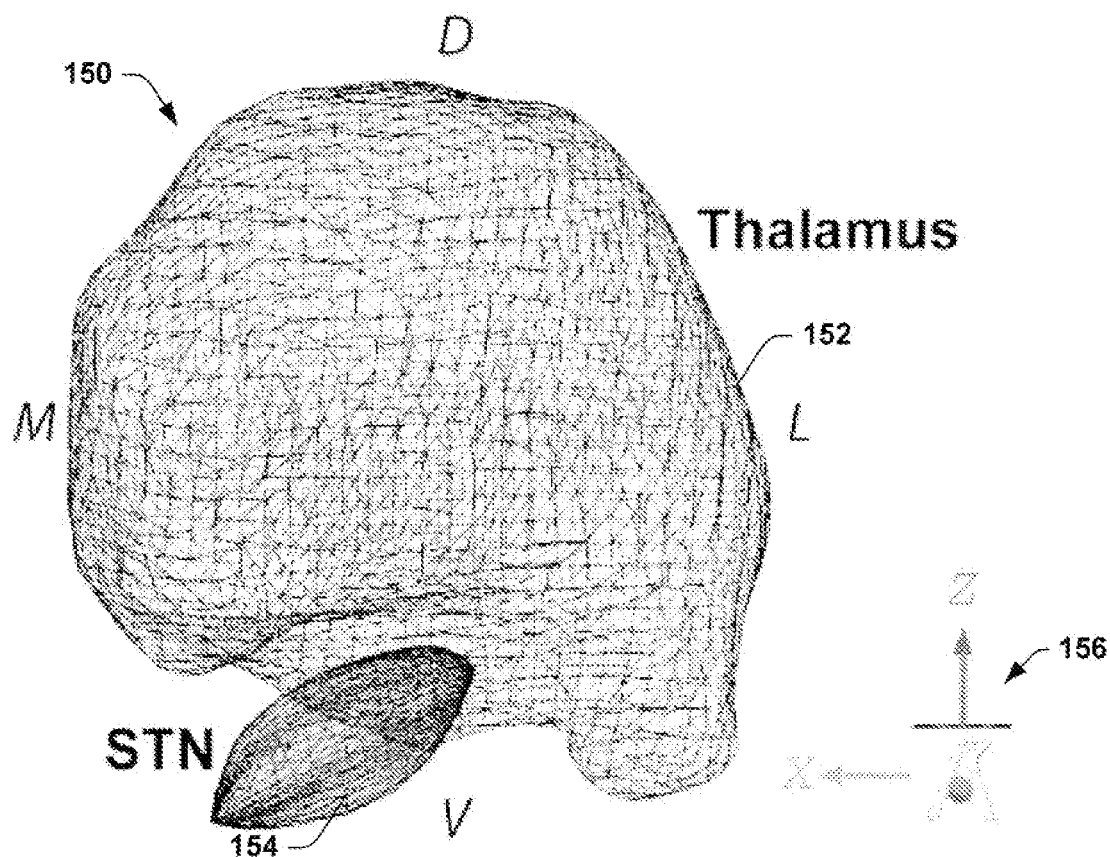
FIG. 3 depicts an example of a representation of a brain atlas formed by a three-dimensional polygonal surface that can be utilized in a method implemented according to an aspect of the invention.

As an example, the brain atlas data 104 can define a 3D surface representation in the form of polygons, such as the representation 150 depicted in FIG. 3. In FIG. 3, the brain atlas 150 includes a plurality of polygons that define surfaces of the brain, including the surfaces of thalamus 152 and the subthalamic nucleus 154. Other nuclei and features can also be represented similarly by generating corresponding brain atlas data. The particular features explicitly mapped in a given atlas may vary according to the potential electrode targets, for example. Also depicted in the brain atlas representation 150 is a reference coordinate system 156, such as may correspond to a stereotactic coordinate system in which the patient's brain is located.

Returning to FIG. 2, it will be understood that the image data 116 corresponds to a pre-operative representation of the patient's brain. Consequently, the brain atlas data 104 also represents a pre-operative mapping of the brain features. Part of a neurosurgical planning and DBS electrode implantation procedure includes forming a burr hole in the cranium of the patient, which can cause brain shift. Brain shift can result in anatomical features (e.g., nuclei) being deformed or shifting anywhere from about 1 mm up to about 1 cm. However, the brain atlas data 104 does not adequately account for such brain shift. Existing techniques, such as AC-PC scaling and user-defined fittings, can be time consuming, introduce error or may be otherwise non-reproducible.

The brain atlas transformation engine 102 is programmed to perform an automated method that fits the brain atlas data 104 based on intra-operative patient-specific neurophysiological data. In the example of FIG. 2, the neurophysiological data corresponds to MER data 106, such as can be obtained intra-operatively using a microelectrode, schematically indicated at 122, implanted within the brain of the patient 101. The microelectrode 122 can be implanted into the patient using a navigation system 124, such as including a stereotaxis (or stereotactic) system and associated visualization system that includes one or more display 128. A variety of suitable navigation systems and stereotactic neurosurgical frames are commercially available from vendors, such as Medtronic Inc. and Elekta Corp. of Stockhom, Sweden, as well from others.

The navigation system 124 employs a three-dimensional coordinate system that is utilized to selectively position the microelectrode 122 at known coordinates in the patient's brain. The microelectrode 122 can provide an electrical signal (or signals) corresponding to electrical activity of adjacent neurons. An example of a microelectrode includes platinum-iridium electrodes, such as are commercially available from FHC Inc. of Bowdoinham, Me. The MER signals are acquired by a microelectrode acquisition system 130, which can store a digital representation of the electrical activity from the electrode. The acquisition system 130 can also provide a corresponding amplified representation of the electrical activity to a display (e.g. a window in the display 128) and to an audio speaker (not shown) so that the surgical personnel can visualize and hear the neuronal activity for the MER site where the recording is made. The microelectrodes can be inserted using a microdrive system, such as the microTargeting™ microdrive available from FHC Inc.

As a further example, the patient 101 can receive a plurality of microelectrode tracks oriented at predetermined angles with respect to the antero-posterior axis (i.e., ring angle) as well as predetermined angles with respect to the medial-lateral axis (i.e., arc angle). The MER acquisition system 130 can record electrical activity for a plurality of MER sites for each of the tracks. Each MER site can be neurophysiologically identified (or classified) intra-operatively by an MER classifier 126. The MER classifier 126 can be implemented as an automated algorithm, such as can be programmed to classify the MER site based on the frequency and amplitude of the spontaneous and motor-evoked neuronal activity recorded at each site. Alternatively or additionally, the MER classifier 126 can be implemented manually by an expertly trained neurophysiologist based on an audible representation of the MER for each site.

The navigation system 124 also provides 3D location information for MER site, such as in the form of a vector representing the electrode location in a stereotactical reference frame (x, y, z). Thus, the MER data 106 thus can include an indication of location in 3D stereotactic space (defined by the navigation system 124) for each MER site and an identification of an anatomical nucleus type for each respective MER site. The location information can be utilized to distinguish between and classify each of the MER recordings as being acquired for a neuron belonging to (e.g., being contained within) specific type of nuclei.

Figure 4:
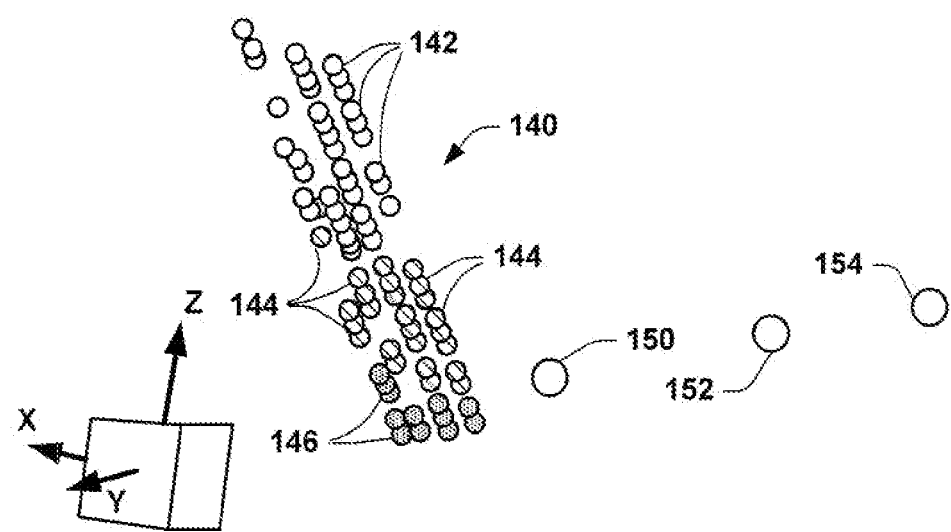
FIG. 4 depicts examples of microelectrode recordings (MER) along a plurality of electrode tracks of a patient that can be collected in a method being performed according to an aspect of the invention.

FIG. 4 depicts a representation 140 of MER recordings can be obtained for a plurality of MER sites along any number of a plurality of distinct electrode tracks for a given patient. Different shading is utilized to identify the different classification of the MER sites, such as determined by the MER classifier 126. In the example of FIG. 4, the unfilled spheres 142 represent thalamic neurons, diagonally striped spheres 144 correspond to subthalamic neurons, and dot-filled spheres 146 represent substantia nigra pars reticulata (SNr). Those skilled in the art will appreciate that color coding can and typically is utilized to distinguish between differently classified MER sites. Also depicted in FIG. 4 are fiducial markers, which include the anterior commissure (AC) 150, the mid-commissural point (MCP) 152, and posterior commissure (PC) 154, which points could also be represented by different colors on a display (e.g., the display 128 of FIG. 2).

Referring back to FIG. 2, the transformation engine 102 is programmed to perform an optimization method that determines a set of transformations that maximize the number of neurophysiologically identified MER sites in their respective atlas-defined nuclei (e.g., the thalamus and STN). The transformation engine 102 is programmed to perform a constrained optimization method to transform (i.e., rotate, translate, and scale) the nuclei of the 3D brain atlas 104 about three orthogonal axes until an optimal location for the entire atlas with respect to the MER data 106 is determined. The optimization method further can be programmed to minimize the inclusion of MER sites for a given nucleus that have been determined to be sites from other nuclei. While in the example of FIG. 2, the optimization is constrained by MER data 106, it is to be understood that other intra-operative or pre-operative data can be utilized as additional or alternative constraints. The transformation engine 102 can apply the resulting transformations to the entire preoperative atlas to generate the intra-operative enhanced atlas data 108.

Figure 5:
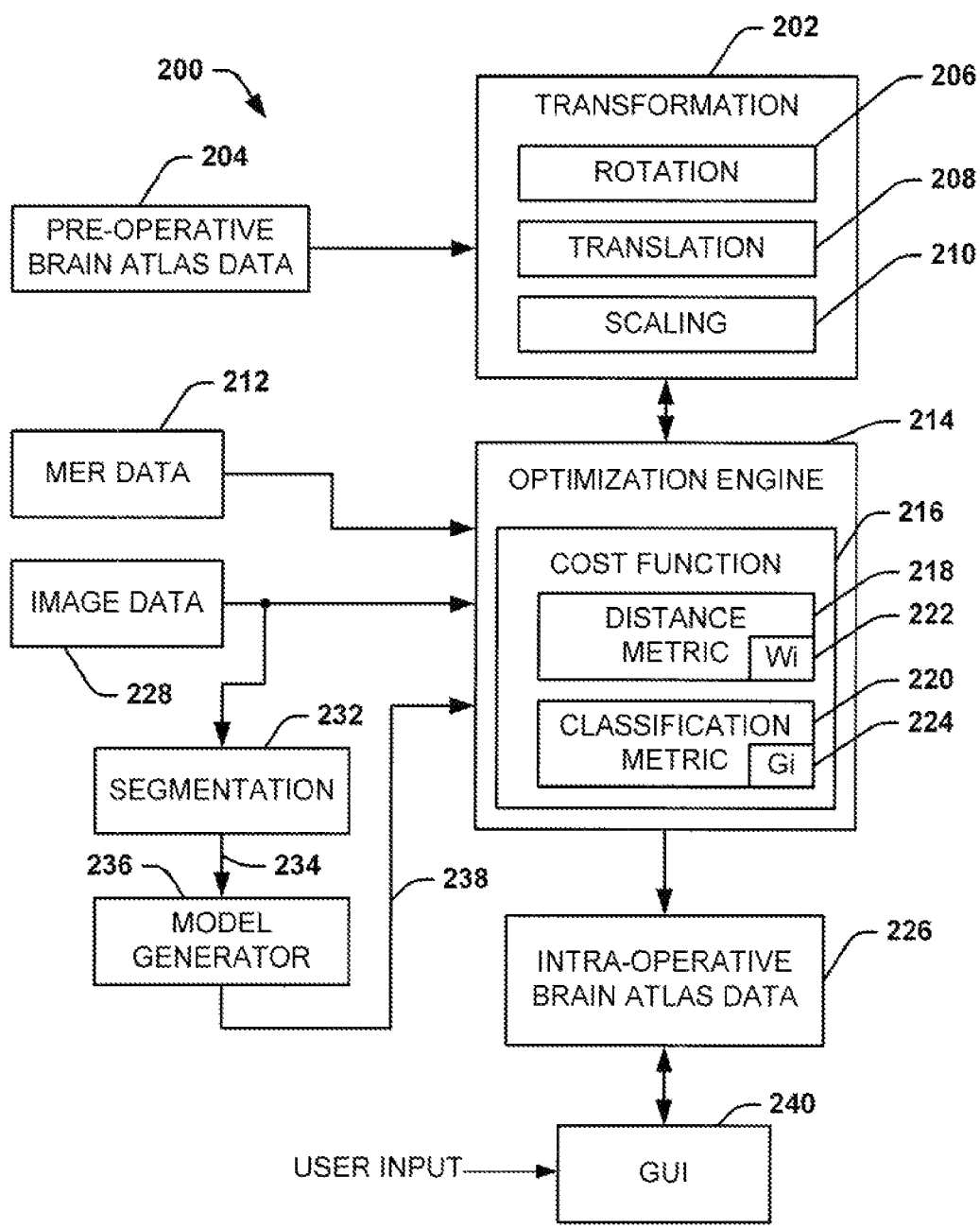
FIG. 5 depicts a functional block diagram of a brain atlas transformation engine according to an aspect of the invention.

As a further example, FIG. 5 depicts a computer-implemented system 200 that can implement a fitting algorithm to fit a brain atlas to intra-operative neurophysiological data (e.g., MER data) according to an aspect of the invention. An optimal transformation can be defined, for instance, as one that maximizes the number of MER sites correctly fitted (i.e., contained) within the atlas nuclei while minimizing both (i) the distance between the atlas and the MER sites not contained by it, and (ii) the number of MER sites fitted incorrectly. It is to be appreciated that other constraints can be employed to refine the parameters of the transformation engine 200.

The system 200 can include a set of predefined transformations 202 that can be applied to preoperative brain atlas data 204. Each of the transformations 202 can be a linear transformation or a non-linear transformation. In the example of FIG. 5, the set of transformations can include rotational transformations 206, translational transformations 208 and scaling transformations 210. Each of these transformations 206, 208 and 210 can be applied to transform the pre-operative brain atlas data 204 to fit intra-operative patient data, which for sake of simplicity will be described as MER data 212. It will be appreciated that the system 200 is not limited to use with MER data, as other types of intra-operative patient data (e.g., OCT generated data) can be utilized additionally or as an alternative. Additionally, as described herein, pre-operative patient data can also be utilized to further constrain the optimization process.

Figure 6:
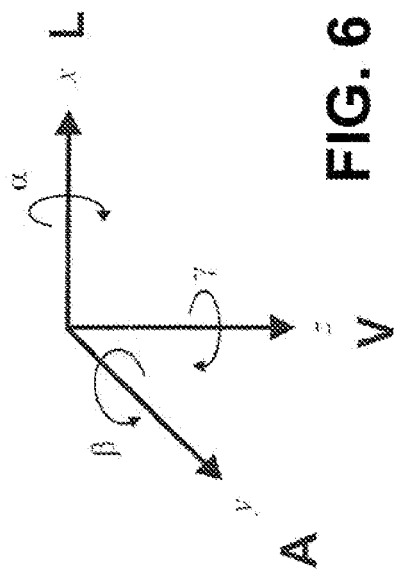
FIG. 6 depicts an example of a coordinate system and associated transformations that can be implemented according to an aspect of the invention.

With reference to FIG. 6, the 3D brain atlas 204 can be transformed to fit the MER data 212 using a set of transformations about the x, y, and z axes. These transformations can include linear transformations, nonlinear transformations, or a combination of linear and nonlinear transformations. With reference to the coordinate system of FIG. 6, the set of transformations 202 can consist of three rotational transformations α, β, and γ (about the x, y, and z axes respectively), translations ($t_x$, $t_y$, and $t_z$), and scaling ($s_x$, $s_y$, and $s_z$) of the three independent axes (FIG. 6) with respect to the mid-commissural point (MCP), which can be identified and marked in a representation of the brain atlas. The transformations 202 can be applied to the brain atlas data 204 as a series of matrix multiplications of the form A'=STA, where A and A' are 4×n matrices (containing the affine coordinates of n vertices forming the atlas surfaces) representing the original and transformed atlases, respectively. T represents the affine transformation matrix that includes rotations (applied sequentially about the y, x, and z axes) and translations; and S represents the scaling matrix transform. For example, T and S can be represented as follows:

$$R = \begin{bmatrix} \cos\beta\cos\gamma - \sin\beta\sin\alpha\sin\gamma & -\cos\beta\sin\gamma + \sin\beta\sin\alpha\cos\gamma & \sin\beta\cos\alpha & t_x \\ \cos\alpha\sin\gamma & \cos\alpha\cos\gamma & -\sin\alpha & t_y \\ -\sin\beta\cos\gamma + \cos\beta\sin\alpha\sin\gamma & \sin\beta\sin\gamma + \cos\beta\sin\alpha\cos\gamma & \cos\beta\cos\alpha & t_z \\ 0 & 0 & 0 & 1 \end{bmatrix}$$

$$S = \begin{bmatrix} s_x & 0 & 0 & 0 \\ 0 & s_y & 0 & 0 \\ 0 & 0 & s_z & 0 \\ 0 & 0 & 0 & 1 \end{bmatrix}$$

The system 200 also includes an optimization engine 214 that is programmed to optimize the set of transformations 202 for fitting the pre-operative brain atlas data 204 to the MER data 212. For instance, the optimization engine 214 includes a cost function 216 that can be optimized to determine the optimal set of the transformations u, 202. In the example of FIG. 2, the cost function 216 includes a distance metric ($g_i(u)$) 218 and a classification metric ($h_i(u)$) 220. The distance metric 218 can include weighting component 222 to provide a weighted distance metric ($W_i g_i(u)$), such as representing a distance between a given MER site and a centroid of a polygon on a surface of from the brain atlas 204. The classification metric 220 can also include a weighting component 224 to provide a weighted classification metric ($V_j h_i(u)$), such as can represent a penalty for fitting a given MER site incorrectly within a nucleus defined by the brain atlas 204.

For example, the cost function $f(u)$ can be defined as a function of a weighted distance metric and weighted classification metric, such as can be expressed as follows:

$$f(u) = \sum_i (W_i g_i(u)^2 + V_i h_i(u)), \qquad \text{Eq. 1}$$

where:
W=weight applied to the distance metric for a given nuclei type that is correctly classified;
i denotes a given nuclei type;
G=weight applied for a given nuclei type that is incorrectly classified; and
u corresponds to the set of transformations.

The set of transformation parameters u can be constrained such that $u_{min} \leq u \leq u_{max}$ (i.e., a constrained optimization). As one example, the optimization may be constrained by allowing a maximum translation of about 10 mm, rotation of about 10 degrees in each direction, and a maximum scaling of ±20% along each axis. In Eq. 1, W and V are weights that allow the user to prioritize the fit of different nuclei, which can be a user programmable value. As an example, the STN weights ($W_1$, $V_1$) can be set to 20 and the weights of the thalamus ($W_2, V_2$) can be set to 2, although other weight values can be utilized.

Those skilled in the art will appreciate that the optimization engine can be performed with other constraint values and weight values. The distance metrics and classification metric further may be expressed as follows:

$$g_i(u) = \sum_j dI_{ij}, \qquad \text{Eq. 2}$$

$$h_i(u) = \sum_l L_{lj}, \qquad \text{Eq. 3}$$

where:
i and l are nuclei indices describing the nucleus type (e.g., STN=1, thalamus=2),
j is a unique index to each MER point; and
$I_{ij}$ and $L_{ij}$ are Boolean operators used to penalize the cost function for missed MER points (e.g., MER point outside its corresponding nucleus) and MER fitted within an incorrect nucleus.

As a further example, to calculate the distance between the MER data and their corresponding nuclei, it is first determined if the MER site was contained within its corresponding nucleus (e.g., based on the classification provided by the MER classifier 126 of FIG. 1). For each correctly classified MER site, the distance metric 218 determines the surface polygon closest to each MER site. The distance metric 218 can compute such distance by measuring the distance from the MER site to each polygon centroid.

For example, the distance metric 218 can be programmed to compute the Euclidean distance from the MER site ($MER_j$) to each polygon centroid ($C_{ij}$), although other distance metrics may be utilized. Eq. 4 is an example, of the Euclidean distance metric that can be utilized to compute the distance.

$$d = \sqrt{(MER_j - C_{ij})^2} \qquad \text{Eq. 4}$$

where the centroid for a given polygon can be determined as follows:

$$C_{ik} = (V_{1ik} + V_{2ik} + V_{3ik})/3 \qquad \text{Eq. 5}$$

where
$V_m$=Polygonal vertex m
i,l=Nucleus type (e.g., l=thalamus, 2=STN, etc.)
j=MER site number
k=Closest polygon on nucleus i to MER j For this polygon, the optimization then computes the angle between the vector formed from the MER point $MER_j$ to the centroid of the polygon and the vector normal to the polygon (N). This calculation of the angle can be expressed as follows:

$$\theta = \cos^{-1}\left(\frac{d^2}{\|d^2\|} \cdot \frac{N_{ij}}{\|N_{ij}\|}\right) \qquad \text{Eq. 6}$$

where the normal $N_{ik}$ of that polygon can be calculated as follows:

$$N_{ik} = (V_{3ik} - V_{1ik}) \times (V_{2ik} - V_{1ik}) \qquad \text{Eq. 7}$$

where $V_{1ik}$, $V_{2ik}$, and $V_{3ik}$ are vertices of the polygon.

Based on the results of Eq. 5, if θ is less than or equal to approximately 90 degrees, the MER site ($MER_j$) is determined to be contained within nucleus i (FIG. 7), and the atlas 204 did not need to be modified for the respective polygon. That is, if $\theta_1$ is less than or equal to approximately 90 degrees, the MER is presumed to be contained within the nucleus and did not contribute to the fit error (e.g., by setting $I_{ij}=0$ for Eq. 2), such that it does not contribute to the cost function. If $\theta_1$ is more than 90 degrees, it is determined that the MER site $MER_j$ is outside its nucleus and its distance to the nucleus surface was added to the cost function of Eq. 2 (e.g., by setting $I_{ij}=1$). This condition can be expressed as follows:

$$p(ij, ik) = \begin{cases} 0, & \text{if } \theta_1 \leq 90° \\ 1, & \text{if } \theta_1 > 90° \end{cases} \qquad \text{Eq. 8}$$

Figure 7:
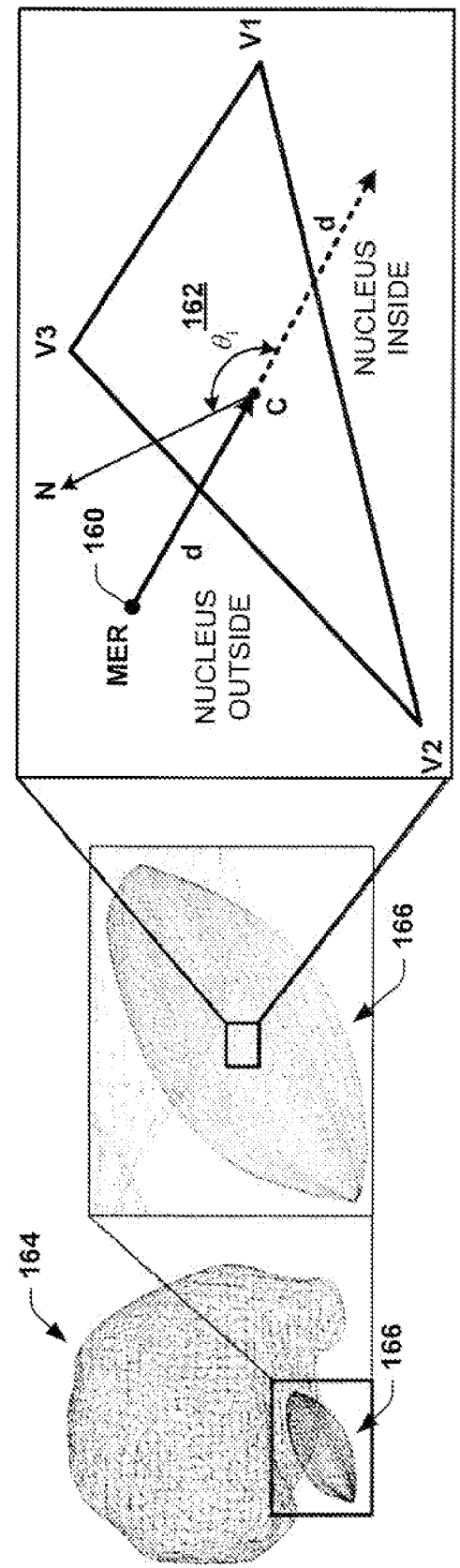
FIG. 7 depicts a schematic representation of a MER site and a closest polygon on the surface of a corresponding atlas nucleus that can be ascertained according to an aspect of the invention.

FIG. 7 depicts a schematic representation of an STN MER site 160 and its closest polygon 162, which have been enlarged from a brain atlas model 164 on the surface of the atlas STN 166. In FIG. 7, the plane of the polygon 162 is given by the three vertices V1, V2, and V3. The surface of defined by this polygon 162 separates the inside and outside of the nucleus with respect to the MER site 160. In this example, the MER site is outside the nucleus because the angle $\theta_1$ between the vector normal (N) to the surface polygon, and the distance vector (ad) defined by the MER site and the polygon centroid (C) is greater than 90 degrees.

Additionally, as mentioned above, the weighted sum of MER sites incorrectly contained by any nucleus can be added to the cost function (of Eq. 2) to penalize atlas transformations that result in incorrect fits, such as according to Eq. 3. Additionally or alternatively, atlas transformations that resulted in nuclei containing MER points of a type other than their own (e.g., STN MER points contained within the thalamus) can result in penalties to the cost function 216. For example, the cost function for this atlas transformation can be increased by a factor of $V_i$ (by setting $L_{ij}=1$ of Eq. 3) if the MER was contained within nucleus (i.e., angle≤90 degrees). The cost function was not penalized (e.g., by setting $L_{ij}=0$ of Eq. 3) if the MER was outside the nucleus (i.e., angle>90 degrees).

Those skilled in the art will understand and appreciate different weighting values that can be utilized, which may be fixed values or be variable parameters. Additionally, there can be more than two weight values for different nuclei (e.g., weight values can be associated with other identifiable anatomical nuclei in addition to the thalamus and STN).

The optimization engine can apply the cost function and its constituent parts for each of the MER sites and ascertain an optimal set of transformations to apply to the original brain atlas data 204. The system 200 in turn applies the optimal transformation set to the brain atlas 204 to generate the enhanced intra-operative brain atlas 226.

By way of further example, the optimization algorithm can be implemented using the Matlab® Optimization Toolbox's fmincon function (The MathWorks Inc., Natick, Mass.), which finds a local minimum of a constrained nonlinear multivariable function using sequential quadratic programming (SQP). Details on SQP are well known and can be found in the literature, including, for example, in Fletcher, R., 1987, *Practical Methods of Optimization*, John Wiley and Sons, and in Gill, P. R., Murray, W., Wright, M. H., 1981, *The Levenberg-Marquardt Method Practical Optimization*, Academic Press, London, pp. 136-137. The optimization can be initialized by using the conventional AC/PC fit for a given patient, although other initial parameters can be utilized. Optimization was performed for a maximum number of iterations and function evaluations, with a constraint tolerance (e.g., of 0.1), an objective function optimality tolerance (e.g., of approximately 0.1) and a transformation parameters tolerance (e.g., of approximately 0.01). The parameter search direction, such as can be given by the second derivative of the cost function (also known as Hessian), can be updated according to the steepest descent method, although other searching methods can be utilized. All other optimization parameters can set to their default values, which can vary according to the software being utilized.

While the example approach discussed above is described as being performed by fitting the brain atlas to the MER data 212, it will be appreciated that other patient-specific data can be utilized to constrain the optimization. For example, as described herein, the optimization engine 214 may be programmed to perform the fitting based on both MER data and image data 228 acquired for the specific patient. The image data, for example, can be magnetic resonance imaging (MRI) data for the patient that was obtained pre-operatively. Other imaging modalities can also be utilized, such as those described herein.

As a further example, the system 200 can include a segmentation module 230 that segments the patient-specific image data to identify one or more different anatomical structures or voids. Some non-limiting examples of different structures or voids that can be segmented from the image data 228 for the patient's brain include ventricles, the thalamus, the striatum, and the globus pallidus. The segmentation can be performed according to a variety of different segmentation algorithms, including those performed by commercially available image processing software or the segmentation can be customized for a given system 200. Examples of some known automated segmentation methods that can be utilized are edge detection methods, region growing methods, curve propagation methods, watershed transformations and the like. The segmentation module 232 provides corresponding three-dimensional segmented image data 234 to a model generator 234.

Figure 8:
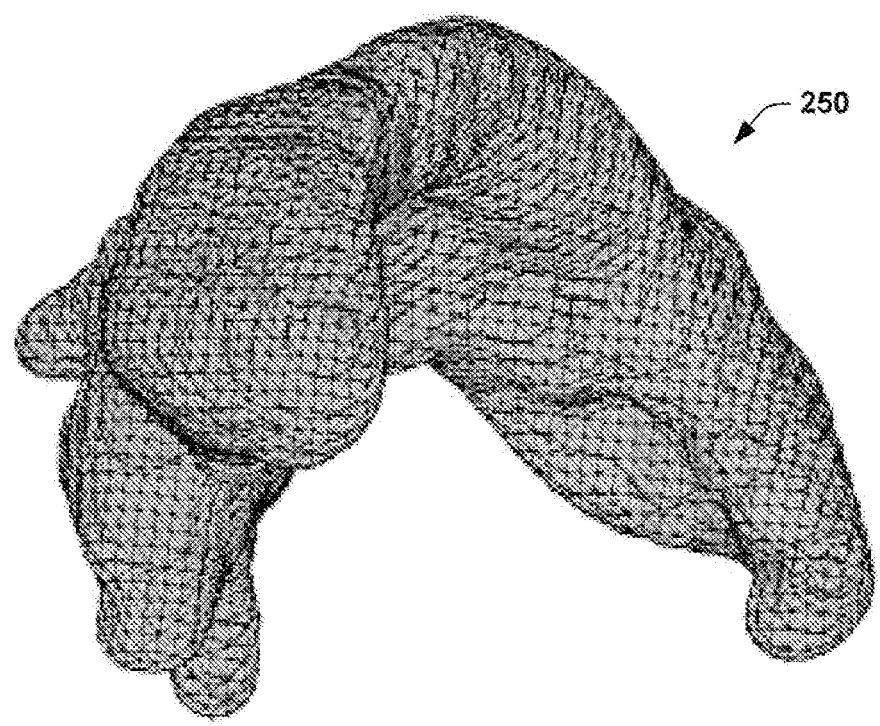
FIG. 8 depicts an example of a three dimensional ventricle model that can be used in accordance with an aspect of the invention.

The model generator 234 can be programmed to generate a three-dimensional surface model for all or a subset of the segmented volumes based on the segmented image data. For example, the segmented image data can be converted into a representation of the segmented structures, such as in the form of a plurality of polygons that define surfaces or boundaries of the segmented structures of the patient's brain. FIG. 8 depicts an example of three-dimensional model of the ventricle, indicated at 250, such as can be generated according to a segmented MRI. Fiducial markers from the patient image data 228 can be identified relative to the model, which can be employed as points utilized to further constrain the cost function 216 similar to as described herein with respect to the MER sites. For example, the optimization engine 214 can finds an affine transformation that maximizes the number of neurophysiologically-identified MER points in their appropriate atlas nuclei while minimizing the number of MER points fitted incorrectly, such as described above with respect to Equations 1-8. The resulting optimized transformation based on the image data 228 can be aggregated with the transformation determined from intra-operative patient data and thereby improve the overall fit of the brain atlas to the stereotactic coordinates of the patient. The cost function used in the optimization further can be normalized accordingly to the number of MER sites for each nucleus.

Figure 9:
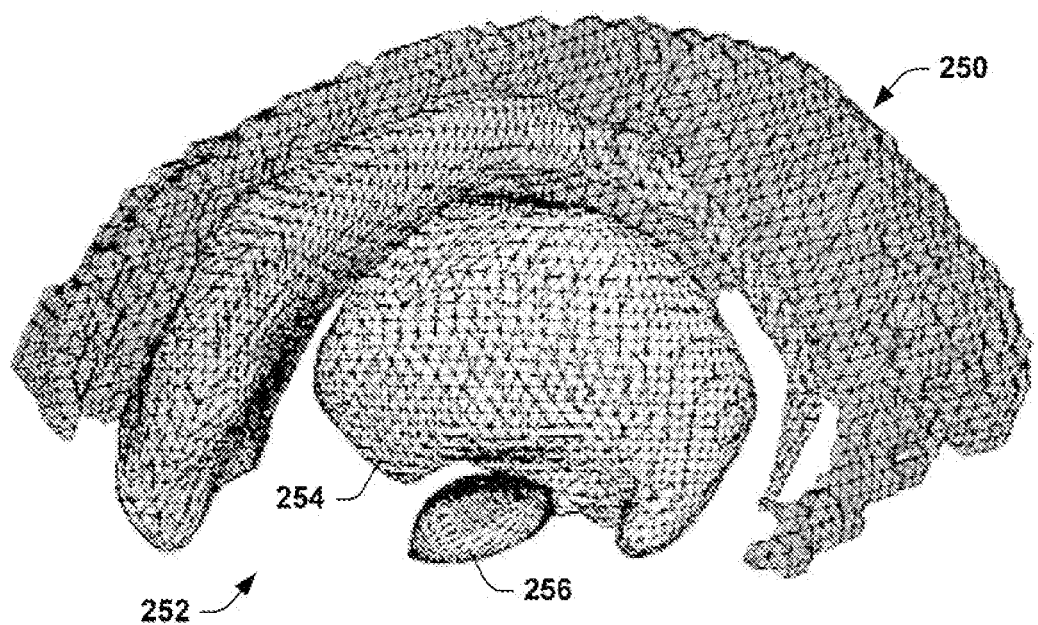
FIG. 9 depicts a representation of the ventricular model of FIG. 8 mapped onto a three-dimensional brain atlas in accordance with an aspect of the invention.
Figure 10:
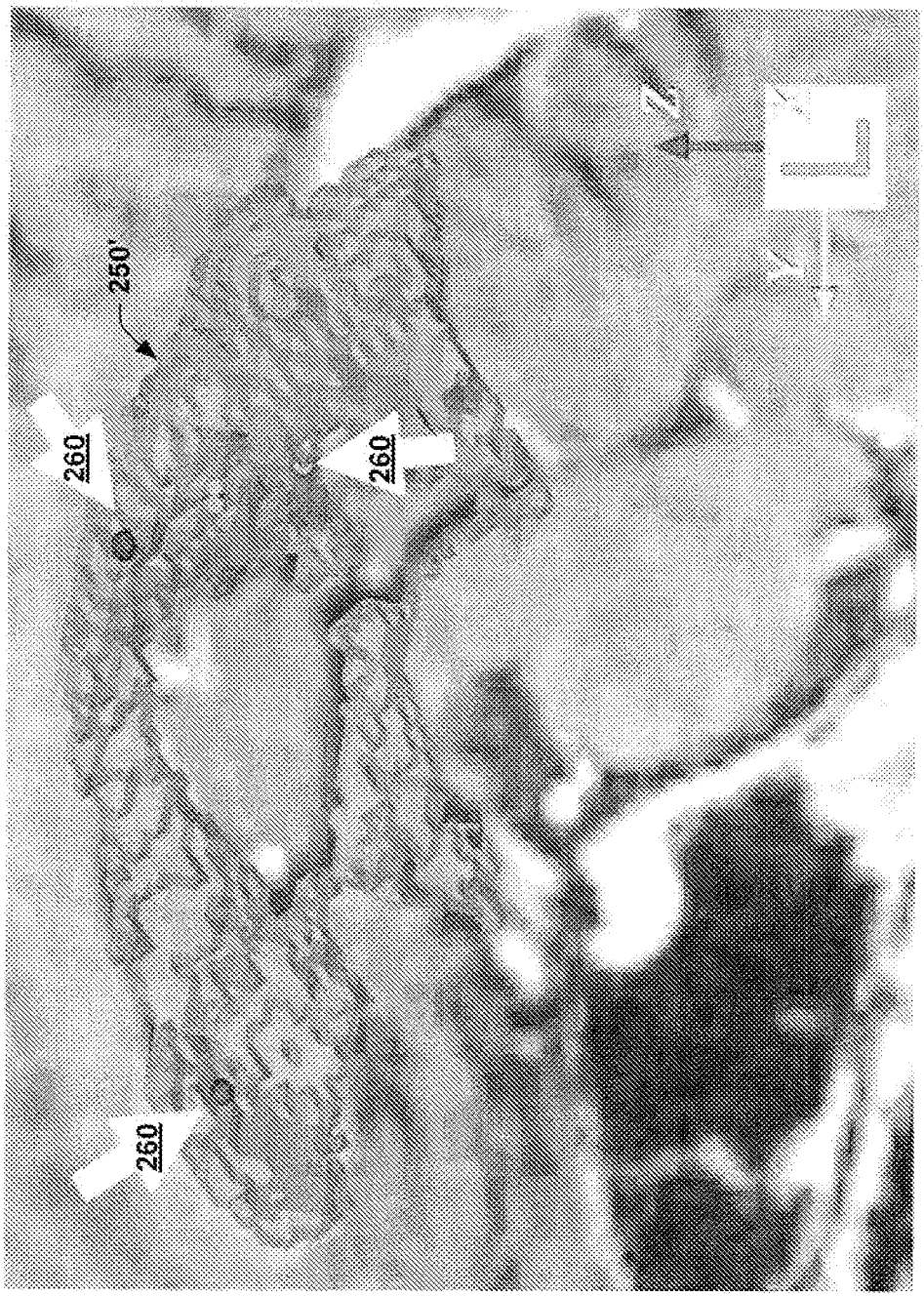
FIG. 10 depicts post-transformation in which the overlap between the ventricular model and the brain atlas has been minimized in accordance with an aspect of the invention.

The transformation can be further constrained by minimizing the overlap between atlas volumes and the co-registered image model 238 that is provided by the model generator 236. An example of the model 250 co-registered into a coordinate system with a brain atlas 252 that includes the thalamus 254 and STN 256 is depicted in FIG. 9. It will be appreciated that the distance metric 218 of the cost function 216 can be computed with respect to one or more points on the surface of the model and the centroid of the brain atlas similar to as discussed above with respect to the MER sites. As an example, the points for a segmented ventricular model can correspond to selected markers located at the surface of the caudate nucleus and thalamus, such as demonstrated by arrows 260 in FIG. 10. Alternatively, since the model can be represented as polygonal surfaces, the centroids of the model surfaces can be utilized and locations of the sites can correspond to points on the surface of the atlas volume for computing the optimized transformation 202 that minimizes overlap between atlas volumes and the co-registered image model 236. Since the optimization can be further constrained, such as by minimizing overlap between the atlas volume and patient-specific image data, the resulting transformation for the brain atlas can be enhanced further.

The system 200 can also include a graphical user interface (GUI) that 240 allows a user to manually adjust the brain atlas, such as relative to a stereotactic framework in which the patient's brain has been position. For example, the GUI 240 can allow microadjustments of the brain atlas, including adjustments in translation, scaling and rotation in each dimension of space. As a result, the GUI 240 can provide means to allow the user to make microadjustments (e.g., fractions of micrometers) along nine degrees of freedom. As an example, the translation adjustments can include a graphical or numerical adjustment element to provide for anterior-posterior (AP), dorsal-ventral (DV) and medial-lateral (ML) adjustments. Similarly, scaling adjustments can be made via the GUI 240 (positive and/or negative scaling) in the AP, DC and ML directions. Additionally, microadjustments can also be made to the resulting brain atlas by rotating the altas in three-dimensional coordinate system of the stereotactic framework, such as including selectable amounts of rotation about the X, Y, and Y axes. The adjustments in the brain atlas can be saved, such as by employing a button, drop down menu or other mechanism associated with the GUI 240.

The GUI 240 can also provide a button or other user-input element that enables a user to perform the automated fitting based on the intra-operative neurophysiological data (e.g., MER and/or OCT data), the segmented image data or a combination of the neurophysiological data and segmented image data for the patient. Those skilled in the art will understand various tools and features that can be combined with the GUI 240 to facilitate fitting the brain atlas to the stereotactic framework. The GUI can further be employed to identify and refine the target location and trajectory for electrode implantation.

Figure 11:
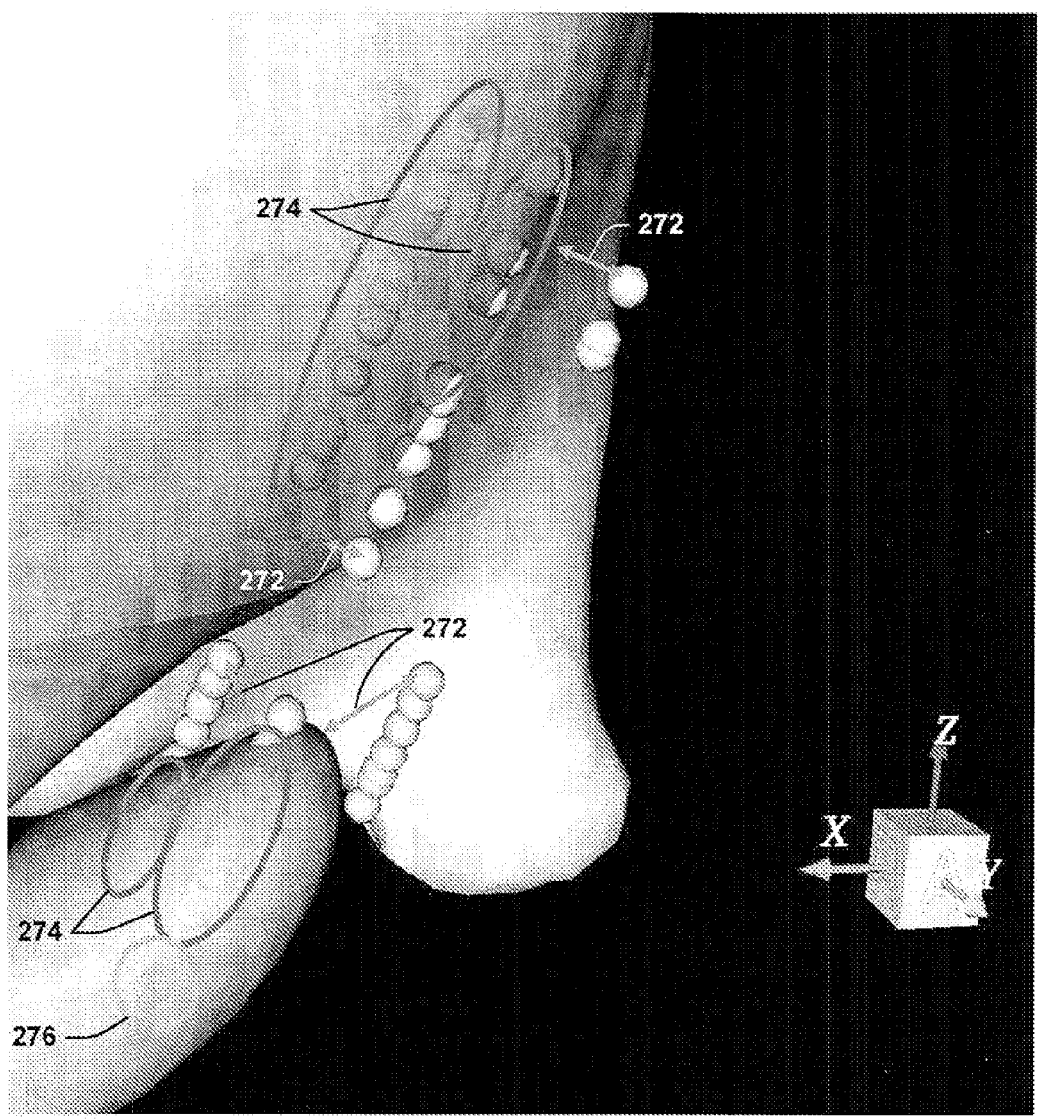
FIG. 11 is an example a brain atlas fit to MER data demonstrating the goodness of the fit according to an aspect of the invention.
Figure 12:
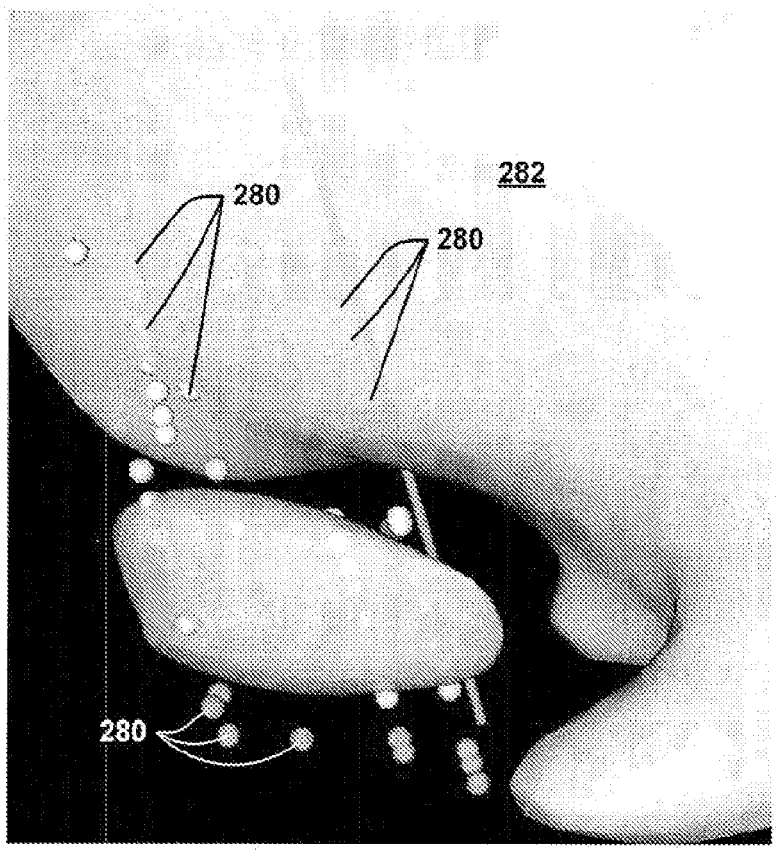
FIG. 12 depicts MERs superimposed on an enhanced three-dimensional brain atlas according to an aspect of the invention.
Figure 13:
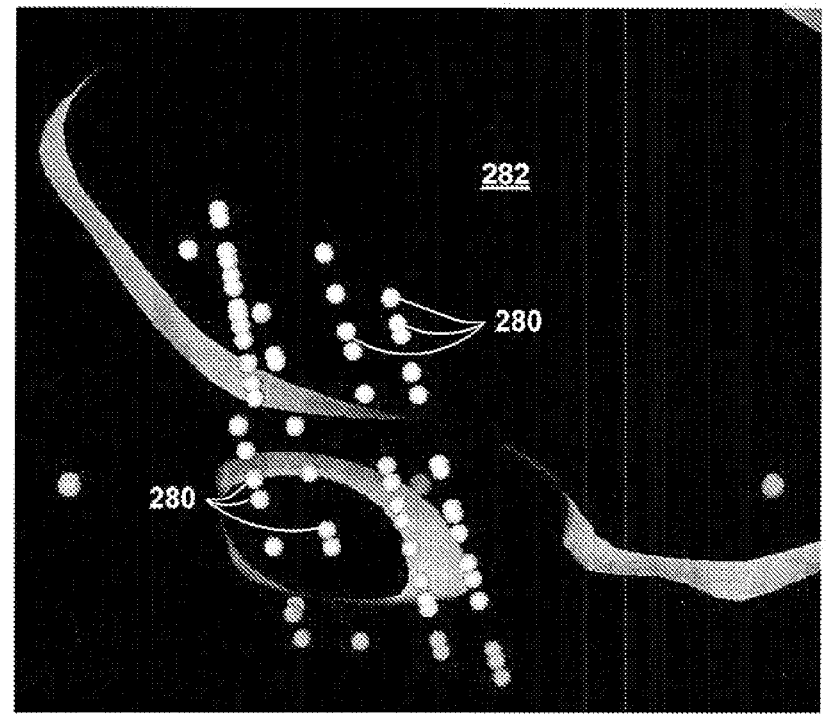
FIG. 13 depicts MER superimposed on a two-dimensional slice of an enhanced brain atlas (with a different contrast than FIG. 12) according to an aspect of the invention.

By way of illustration, FIG. 11 depicts an example of an image 270 demonstrating the summed distance from unfitted MER to atlas, indicated at 272. Also shown in FIG. 7 are MER 274 correctly fitted (i.e., contained) within respective nuclei, indicated by circular markings 274, and MER incorrectly fitted within atlas, indicated by circular marking 276. As a further illustration, FIGS. 12 and 13 demonstrate examples MER recordings 280 superimposed on to different representations of a given brain atlas 282, which had been transformed according to an aspect of the invention.

Figures 14, 15:
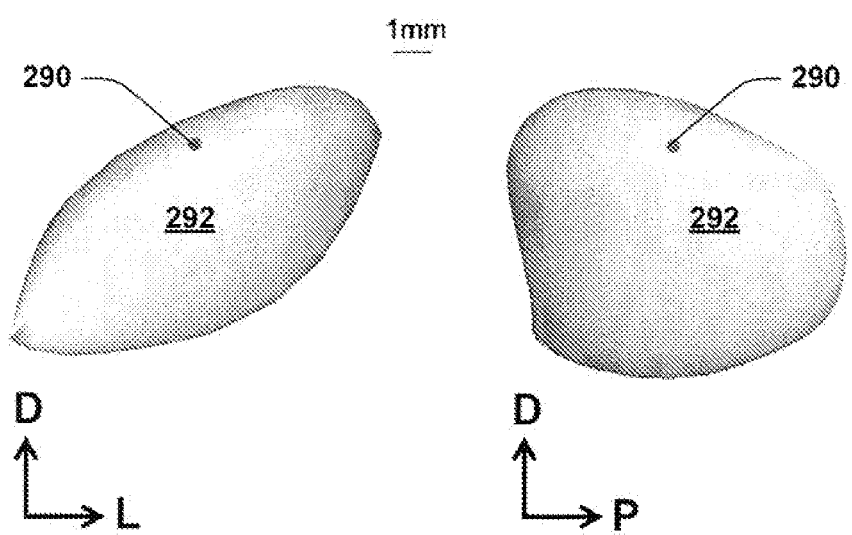
FIG. 14 depicts an example of a DBS electrode target that can be determined according to an aspect of the invention.
FIG. 15 depicts a different view of the DBS electrode target of FIG. 14.

Referring back to FIG. 2, the target predictor 110 can determine the one or more electrode target locations in the enhanced atlas system 100. For example, FIGS. 14 and 15 demonstrate a predicted target electrode location 290 defined in the dorso-medial STN 292. FIG. 14 depicts a coronal view of the STN and FIG. 15 depicts a saggital view of the STN 292. Also depicted in FIGS. 14 and 15, are axes demonstrating dorso-lateral (D-L) and dorso-posterior (D-P) directions.

The target location 290 (FIGS. 14 and 15) can be automatically refined for the given patient 101 when the brain atlas data 104 is fitted to the MER data 106 according to an aspect of the invention. The trajectory calculator 112 can compute a corresponding trajectory to the target location in the enhanced atlas data 108. The trajectory from the burr hole to the 3D target location in the stereotactic coordinate system can be optimized, for example, based on the atlas data 108 and the image data 116 acquired for the patient 101. The trajectory, oriented at a double oblique angle, can be specified in the enhanced atlas, such as by defining arc and ring angles of the stereotactic frame (from the sagittal plane and anterior-posterior direction, respectively) that avoid the ventricles, sulci, and major arteries.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware, such as shown and described with respect to the computer system of FIG. 16. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 16:
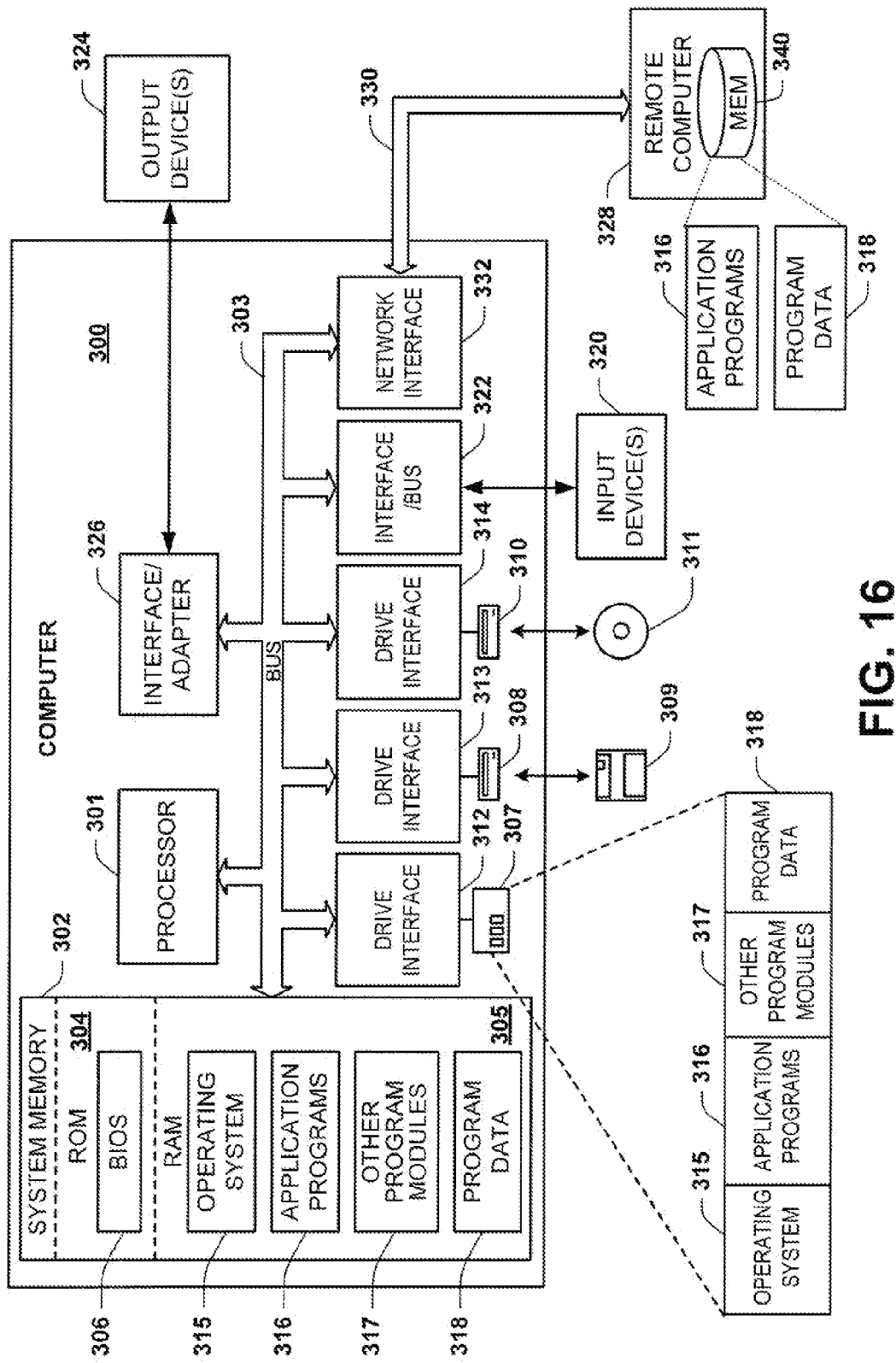
FIG. 16 depicts an example of computer system environment that can be utilized to implement a method according to an aspect of the invention.

In this regard, FIG. 16 illustrates one example of a computer system 300 that can be employed to execute one or more embodiments of the invention by storing and/or executing computer executable instructions. Computer system 300 can be implemented on one or more general purpose networked computer systems, embedded computer systems, routers, switches, server devices, client devices, various intermediate devices/nodes or stand alone computer systems. Additionally, computer system 300 can be implemented on various mobile clients such as, for example, a personal digital assistant (PDA), laptop computer, pager, and the like, provided it includes sufficient processing capabilities.

Computer system 300 includes processing unit 301, system memory 302, and system bus 303 that couples various system components, including the system memory, to processing unit 301. Dual microprocessors and other multi-processor architectures also can be used as processing unit 301. System bus 303 may be any of several types of bus structure including a memory bus or memory controller, a peripheral bus, and a local bus using any of a variety of bus architectures. System memory 302 includes read only memory (ROM) 304 and random access memory (RAM) 305. A basic input/output system (BIOS) 306 can reside in ROM 304 containing the basic routines that help to transfer information among elements within computer system 300.

Computer system 300 can include a hard disk drive 307, magnetic disk drive 308, e.g., to read from or write to removable disk 309, and an optical disk drive 310, e.g., for reading CD-ROM disk 311 or to read from or write to other optical media. Hard disk drive 307, magnetic disk drive 308, and optical disk drive 310 are connected to system bus 303 by a hard disk drive interface 312, a magnetic disk drive interface 313, and an optical drive interface 314, respectively. The drives and their associated computer-readable media provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the present invention.

A number of program modules may be stored in drives and RAM 305, including operating system 315, one or more application programs 316, other program modules 317, and program data 318. The application programs and program data can include functions and methods programmed to fit a brain atlas to MER data, such as shown and described herein.

A user may enter commands and information into computer system 300 through one or more input devices 320, such as a pointing device (e.g., a mouse, touch screen), keyboard, microphone, joystick, game pad, scanner, and the like. For instance, the user can employ input device 320 to edit or modify a domain model. Additionally or alternatively, a user can access a user interface via the input device to create one or more instances of a given domain model and associated data management tools, as described herein. These and other input devices 320 are often connected to processing unit 301 through a corresponding port interface 322 that is coupled to the system bus, but may be connected by other interfaces, such as a parallel port, serial port, or universal serial bus (USB). One or more output devices 324 (e.g., display, a monitor, printer, projector, or other type of displaying device) is also connected to system bus 303 via interface 326, such as a video adapter.

Computer system 300 may operate in a networked environment using logical connections to one or more remote computers, such as remote computer 328. Remote computer 328 may be a workstation, computer system, router, peer device, or other common network node, and typically includes many or all the elements described relative to computer system 300. The logical connections, schematically indicated at 330, can include a local area network (LAN) and a wide area network (WAN).

When used in a LAN networking environment, computer system 300 can be connected to the local network through a network interface or adapter 332. When used in a WAN networking environment, computer system 300 can include a modem, or can be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

What have been described above are examples and embodiments of the invention. It is, of course, not possible to describe every conceivable combination of components or methodologies for purposes of describing the invention, but one of ordinary skill in the art will recognize that many further combinations and permutations of the present invention are possible. Accordingly, the invention is intended to embrace all such alterations, modifications and variations that fall within the scope of the appended claims. In the claims, unless otherwise indicated, the article "a" is to refer to "one or more than one."

What is claimed is:

1. A method comprising:
   storing in memory pre-operative brain atlas data that defines a plurality of nuclei of an atlas space;
   intra-operatively obtaining neurophysiological data for a plurality of known sites in a brain of a given patient to provide corresponding intra-operative neurophysiological data for at least a portion of the sites;
   performing, by a computer processor, a constrained optimization to fit the preoperative brain atlas data based at least in part on the intra-operative neurophysiological data;
   wherein the constrained optimization includes maximizing a number of the at least the portion of the sites that are correctly fitted to the atlas space on a nucleus by nucleus basis with respect to the nuclei defined in the pre-operative brain atlas data, and generating an enhanced brain atlas based on a transformation derived from the constrained optimization; and
   adjusting the transformation relative to at least one axis of stereotactic coordinate system for the given patient.

2. The method of claim 1, wherein the intra-operative neurophysiological data comprises microelectrode recordings (MER) for a plurality of MER sites.

3. The method of claim 2, wherein the intra-operatively obtaining of the neurophysiological data further comprises:
   acquiring the MER as MER data for a plurality of MER sites in the brain of the given patient, each of the plurality of MER sites having a known location in a stereotactic coordinate system;
   classifying an anatomical location for at least a substantial portion of the plurality of MER sites based on respective MER data; and
   providing classified MER data based on the classifying to define the intra-operative neurophysiological data for the at least a substantial portion of the plurality of MER sites.

4. The method of claim 3, wherein the classifying is performed by an computer implemented classification method to provide the classified MER data, the classified MER data being utilized to constrain the constrained optimization that is performed.

5. The method of claim 3, wherein the classifying is performed by an expert person to provide classified MER data, the classified MER data being utilized to constrain the constrained optimization that is performed.

6. The method of claim 3, wherein the sites are microelectrode recording (MER) sites.

7. The method of claim 6, wherein the constrained optimization is programmed to minimize at least one of (i) a distance between the brain atlas and the MER sites not contained by the nuclei of the brain atlas and (ii) the number of known sites fitted incorrectly according to the pre-operative brain atlas data.

8. The method of claim 7, wherein, for each MER site, the constrained optimization is further programmed to determine if the MER site was contained within its corresponding nucleus by locating a surface polygon that is closest to each MER site and by measuring the distance from the MER site to each polygon centroid.

9. The method of claim 8, wherein, for each MER site, the method further comprises:
   calculating a vector normal to the surface polygon that includes the polygon centroid of the closest polygon;
   calculating a distance vector corresponding to the measured distance from the MER site to the closest polygon centroid; and
   computing an angle between the vector normal to the surface polygon and the distance vector that includes the closest polygon normal.

10. The method of claim 1, wherein the constrained optimization is further programmed to minimize a cost function feu) expressed as:

$$f(u) = \sum_i (W_i g_i(u)^2 + V_i h_i(u))$$

where:
   $g_i(u)$ is a distance metric corresponding to a distance between the plurality of known sites and a surface of nuclei represented in the pre-operative brain atlas data;
   $h_i(u)$ is a classification metric that indicates of the sites incorrectly fit to a surface of nuclei represented in the pre-operative brain atlas data;
   W=weight applied to the distance metric gi for a given nuclei type that is correctly classified;
   V=weight applied for a given nuclei type that is incorrectly classified:
   i denotes a given nuclei type; and
   u corresponds to a set of transformations being applied to fit the pre-operative brain atlas data to the intra-operative neurophysiological data.

11. The method of claim 1, wherein the constrained optimization is further constrained according to pre-operative patient specific data.

12. The method of claim 11, wherein the pre-operative patient specific data that constrains the optimization further comprises image data acquired from the given patient according to an imaging modality.

13. The method of claim 12, wherein the image data comprises a segmented surface model that is co-registered with the intra-operative neurophysiological data into a stereotactic coordinate system of the pre-operative brain atlas data.

14. The method of claim 1, wherein at least a portion of the plurality of known sites are identified by data obtained for the brain of the given patient intra-operatively using optical coherence tomography.

15. The method of claim 1, further comprising:
   adjusting the transformation relative to at least one axis of stereotactic coordinate system for the given patient in response to a user input.

16. The method of claim 1, wherein constrained optimization employed to fit the preoperative brain atlas data to the intra-operative neurophysiological data comprises one of a linear or non-linear transformation.

17. The method of claim 1, further comprising:
for each of the at least the portion of the sites, analyzing the intra-operative neurophysiological data of the respective site to identify a respective one of the nuclei to which the respective intra-operative neurophysiological data corresponds, wherein the constrained optimization is based on the identifications.

18. The method of claim 1, wherein:
the intra-operatively obtained neurophysiological data for the at least the portion of the sites identify respective ones of the nuclei defined in the pre-operative brain atlas data; and
the maximizing the number of the at least the portion of the sites that are correctly fitted to the atlas space on the nucleus by nucleus basis with respect to the nuclei defined in the pre-operative brain atlas data includes matching up the respective sites to their respectively identified nuclei.

19. A method comprising:
storing in memory pre-operative brain atlas data that defines a plurality of nuclei of an atlas space;
intra-operatively obtaining neurophysiological data for a plurality of sites in an anatomical region of a patient; and
performing, by a computer processor, a constrained optimization to fit the intraoperatively obtained neurophysiological data to the atlas space, the optimization taking into consideration the definitions of the nuclei to maximize a number of the sites that are correctly fitted to the defined nuclei data, and generating an enhanced brain atlas based on a transformation derived from the constrained optimization; and
adjusting the transformation relative to at least one axis of stereotactic coordinate system for the given patient.

20. A method comprising:
storing in memory pre-operative brain atlas data that defines a plurality of nuclei of an atlas space;
intra-operatively obtaining neurophysiological data for a plurality of sites in an anatomical region of a patient; and
performing, by a computer processor, a constrained optimization to determine a set of transformations that maximizes a number of the sites that are fitted to their respective atlas-defined nuclei data, and generating an enhanced brain atlas based on a transformation derived from the constrained optimization; and
adjusting the transformation relative to at least one axis of stereotactic coordinate system for the given patient.

* * * * *